United States Patent [19]

Haas et al.

[11] Patent Number: 5,158,702
[45] Date of Patent: Oct. 27, 1992

[54] SILYLATED BENZOIC ACID DERIVATIVES II

[75] Inventors: Wolfgang Haas, Germering; Norman Haberle; Rainer Winkler, both of München; Franz-Heinrich Kreuzer, Martinsried, all of Fed. Rep. of Germany

[73] Assignee: Consortium für elektrochemische Industrie GmbH, Münich, Fed. Rep. of Germany

[21] Appl. No.: 542,130

[22] Filed: Jun. 22, 1990

[30] Foreign Application Priority Data

Jun. 22, 1989 [DE] Fed. Rep. of Germany ....... 3920509
Apr. 24, 1990 [DE] Fed. Rep. of Germany ....... 4013045

[51] Int. Cl.$^5$ .................. C09K 19/06; C09K 19/52; C07F 7/04; C07F 7/08
[52] U.S. Cl. ................... 252/299.6; 252/299.01; 252/299.63; 252/299.64; 252/299.66; 252/299.67; 556/431; 556/434; 556/439; 556/453; 556/454; 556/456; 556/457
[58] Field of Search ........... 252/299.01, 299.6, 299.61, 252/299.64, 299.65, 299.66, 299.67; 556/9, 10, 12, 431, 434, 437, 438, 439, 453, 454, 456, 457; 428/1

[56] References Cited

U.S. PATENT DOCUMENTS

Re. 30,554 3/1981 Weinberg et al. .............. 260/429 R
4,981,607 1/1991 Okawa et al. .................. 252/299.01
4,997,591 3/1991 Heppke et al. ................. 252/299.61

FOREIGN PATENT DOCUMENTS 0322703 7/1989 Fed. Rep. of Germany .
0355008 2/1990 Fed. Rep. of Germany .

OTHER PUBLICATIONS

Chemical Abstracts, vol. III, 1989, p. 742, Abstract No. 205667e JP-A 01 144 491 (Toshiba Corp.) Ferroelectric Chiral Smectic Liquid Crystal Materials.
Aquilera, et al., Polymer Bulletin 12, Nov. 1984, Liquid Crystal Polymers, Thermotropic Liquid Crystalline Bimesogenic Molecules with Highly Flexible Oligosiloxane Spacer, pp. 383–388.

Primary Examiner—Robert L. Stoll
Assistant Examiner—Shean C. Wu

[57] ABSTRACT

The present invention relates to compounds of the formula

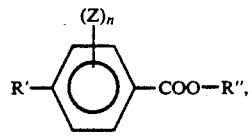

(8)

in which
Z is a radical bonded to the benzene ring in the 2-, 3-, 5- or 6-position, namely a halogen atom, a cyano group or a hydroxyl group,
n is 0, 1 or 2,
R″ is a radical of the formula $$R'''-[Si(R^*)_2](CH_2)_yR''''- \qquad (9),$$

in which
Y is an integer from 4 to 18,
R‴ is as defined in the description,
R* is identical or different, optionally substituted $C_1$- to $C_{18}$-hydrocarbon or hydrocarbonoxy radicals,
R″″ is a radical of the formula —$(E)_z$— which is optionally bonded to the carboxy group via a phenylene or biphenylene radical, where
E is a divalent radical of the formula —O— or —Si(R*)$_2$—, and
Z is the number 0 or 1, and the radical
R′ is a halogen atom, a cyano radical, a cholesteryl radical, a radical as defined for R* or of the formula —$C_6H_4$—R**, and
R** may have any meaning of R*, with the exception of an n-octyloxy or an n-decyloxy radical,
and the preparation and use thereof.

7 Claims, No Drawings

SILYLATED BENZOIC ACID DERIVATIVES II

The invention relates to novel silylated benzoic acid derivatives, some of which are liquid-crystalline, a process for their preparation, and their use.

PRIOR ART

Liquid-crystalline compounds are described, inter alia, by D. Demus, H. Demus and H. Zaschke (Flüssige Kristalle in Tabellen [Liquid Crystals in Tables], 1974; D. Demus and H. Zaschke, Flüssige Kristalle in Tabellen II [Liquid Crystals in Tables II], 1984, VEB-Verlag Leipzig). US-A-4,358,391 (H. Finkelmann et al., Wacker-Chemie GmbH) describes liquid-crystalline polymers having an organopolysiloxane backbone and mesogenic side groups. M. Petrzilka et al. (EP-A-122,389, F. Hoffmann-La Roche & Co.) claim liquid crystal components having an alkenyl chain, it also being possible for a benzoic acid derivative to be attached to this alkenyl chain. These compounds do not contain organosilicon groups. W. R. Young et al. (Molecular Crystals and Liquid Crystals, Vol. 13, pages 305-321, 1971, Gordon and Breach Science o Publishers) report, inter alia, 4'-silylated benzimides of 4-aminophenol benzoates. At the bottom of page 309, they mention that these silicon-containing esters, in contrast to comparable substances, do not form a mesomorphic phase, which is attributed to the steric hinderance of the organosilyl group. JP-A 89/144,491 (laid-open on 6.6.1989, cited in Chemical Abstracts, Vol. 111, 205 667e (1989)) describes the preparation of (R)-4-(3-pentamethyldisiloxypropyloxy)phenyl-4,-(1-methylheptyloxy)biphenyl-4-carboxylate. However, this compound is not stable and tends to lose the Si-bound, propylene group. Further compounds mentioned therein cannot be prepared since they contain non-existent organic groups ($-C_2H_7$ and $-C_6H_{17}$).

OBJECT

The object of the present invention was to synthesize novel, preferably liquid-crystalline compounds, in particular those containing organosilicon groups. It was a further object of the present invention to prepare liquid-crystalline compounds which are readily miscible with other liquid crystals, and are colorless and of low viscosity. It was also an object of the present invention to prepare liquid-crystalline compounds which are highly suitable as dielectrics in display devices and in particular by means of which short addressing times and high contrasts can be achieved in such devices.

DESCRIPTION

The abovementioned objects are achieved by the present invention through compounds of the formula

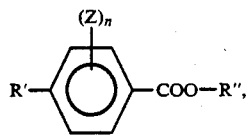

in which
  Z is a radical bonded to the benzene ring in the 2-, 3-, 5- or 6-position, namely a halogen atom, a cyano group or a hydroxyl group,
  n is 0, 1 or 2,
  R" is a radical of the formula

in which
  y is an integer from 4 to 18,
  R''' is a $C_1-$ to $C_8-$alkyl radical, a radical of the formula $R*-[Si(R*)_2O]_v-$, where
    v is an integer having a value of from 1 to 10, or
    a radical of the formula

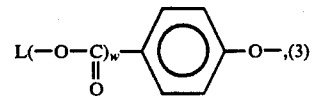

in which
  w is the number 0 or 1, and
  L is a cholesteryl radical or a phenyl radical which is optionally substituted by phenyl, halogen, cyano and/or $C_1-$ to $C_4-$ alkoxy radicals, or, if w=0, may alternatively be a halogen atom, a cyano radical or a $C_1-C_4-$alkoxy radical;
  R* is identical or different, optionally substituted $C_1-$ to $C_{18}-$hydrocarbon or hydrocarbonoxy radicals,
  R'''' is a radical of the formula —E— which is optionally bonded to the carboxyl group via a phenylene or biphenylene radical, where
    E is a divalent radical of the formula —O— or $-[Si(R*)_2]_z-$, where a radical of the formula —O— must not be bonded directly to the oxygen atom of the carboxyl group, and
    z is the number 0 or 1,
  and the radical
  R' is a halogen atom, a cyano radical, a radical as defined for R* or of the formula $-C_6H_4-R**$, where
    R** optionally substituted $C_1-$ to $C_{18}-$hydrocarbon or hydrocarbonoxy radicals, with the exception of an n-octyloxy or an n-decyloxy radical.

n preferably has the value 0 or 1, in particular 0. Preferred substituents for the radicals R* are, in particular, fluorine or chlorine atoms, cyano radicals and oxiranyl radicals.

The present invention also relates to compounds of the formula

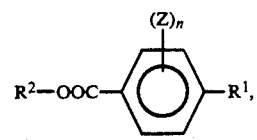

in which
R² is a radical of the formula (22):

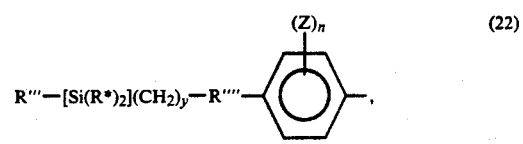

where, in the formulae (1) and (22),
R* is identical or different, optionally substituted $C_1-$ to $C_{18}-$hydrocarbon or hydrocarbonoxy radicals, $R^1$ is a halogen atom, a cyano radical, a radical as defined for $R^{}$, and $R'''$, $R''''$, $R^{}$ and y are as defined in the formula (8) or (9).

Preferred compounds of the formula (1) are those in which $R'''$ is a $C_1$- to $C_4$-alkyl group, preferably a methyl group, and/or $R''''$ is a divalent radical of the formula —O— or a single chemical bond, and/or $R^1$ is a phenyl or cyclohexyl radical which is optionally substituted by $C_1$- to $C_8$-alkyl or alkoxy radicals, or is a $C_1$- to $C_{18}$-alkyl radical or a $C_1$- to $C_{18}$-alkoxy radical, with the exception of n-octy and n-decloxy radicals, it also being possible for the radicals mentioned to be substituted by halogen atoms and trialkylsilyl groups, and/or $R^*$ are methyl groups, and/or n has the value 0, and the other radicals in each case are as defined above in the formula (1).

The abovementioned compounds of the formula (8) or (1) may contain, along their molecular chain, further structural units selected from the group comprising the radicals B, namely the phenylene, cyclohexylene, pyridinediyl, pyrimidinediyl, pyridazinediyl, triazinediyl, tetrazinediyl, dioxanediyl, tetrahydrofurandiyl, bicyclo[2.2.2]octanediyl and cholesteryl radicals, and the radicals D, namely the carbonyloxy, oxycarbonyl, —CH$_2$—CH$_2$—, —O—CH$_2$— and —CH$_2$— groups and radicals of the formulae —CH=CH—, —N=CH—, —CH=N—, —C≡C—, —N=N—, —N=N(O)— and —O—, with the proviso that the abovementioned radicals and groups, if possible, may be substituted by $C_1$- to $C_{18}$-alkyl radicals, phenyl radicals or polar radicals, preferably halogen atoms, cyano groups or hydroxyl groups, and none of the radicals D are linked directly to one another.

The further structural units which extend the chain are preferably selected from the group comprising the 1,4-phenylene, 1,4-cyclohexylene, 2,5-pyridinediyl, 2,5-pyrimidinediy1,3,6-pyridazinediy1,3,6-triazinediyl, 3,6-tetrazinediyl, 2,5-dioxanediyl, 2,5-tetrahydrofurandiyl, bicyclo[2.2.2]octanediyl and cholesteryl radicals and carbonyloxy, oxycarbonyl, —CH$_2$—CH$_2$—, —O—CH$_2$— and —CH$_2$—O— groups, radicals of the formulae —CH=C—, —N=CH—, —CH=N—, —C≡C—, —N=N—, —N=N(O)— and —O—, with the proviso that the abovementioned radicals and groups, if possible, may be substituted by $C_1$- to $C_{18}$-alkyl radicals, phenyl radicals or polar radicals, preferably halogen atoms, cyano groups or hydroxyl groups.

The chain-like compounds according to the invention preferably contain a maximum of four identical or different radicals B which are mentioned above as additional structural units and are, in particular, linked to one another and to the radical of the chain-like compound by a maximum of five of the abovementioned radicals D.

The radicals B and D mentioned above as additional structural units are preferably not substituted or are substituted by hydrogen atoms.

The abovementioned additional structural units B and D are preferably linked to one another in accordance with the formula below:

$-[(B)_b(D)_d]_c$-, where each of the radicals B and D may adopt the abovementioned meanings, with the proviso that none of the radicals D are linked directly to one another, each of the indices b and c is an integer having a value of from 0 to 6, b and c in each case being identical to or different from one another, and d is in each case the number 0 or 1.

Of the abovementioned compounds, the liquid-crystalline compounds are preferred. The present invention includes, if they are usable all enantiomers and diastereomers of the compounds mentioned, individually and in mixtures.

PREPARATION PROCESSES

Process 1

Compounds of the formula (8) or (1) can be prepared by reacting compounds of the formula

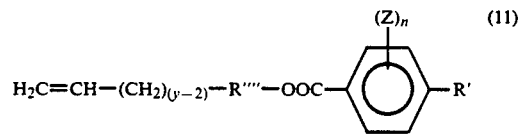

or compounds of the formula

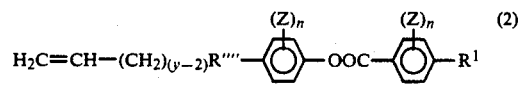

with compounds of the formula

in the presence of platinum metals and/or compounds thereof, where, in the above formulae (2), (11) and (12), n, y, Z, R', R''', R'''' and $R^*$ are as defined in the formula (8) and $R^1$ is as defined in the formula (1).

The platinum metals and/or compounds thereof employed are preferably platinum and/or compounds thereof. All catalysts which have also been employed hitherto for the addition reaction of hydrogen atoms bonded directly to Si atoms with aliphatically unsaturated compounds can be employed here. Examples of such catalysts are metallic and finely divided platinum, which may be on supports, such as silicon dioxide, aluminum oxide or activated charcoal, compounds or complexes of platinum, such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including products of reaction of $H_2PtCl_6 \cdot 6H_2O$ and cyclohexanone, platinum-vinylsiloxane complexes, in particular platinum-divinyltetramethyldisiloxane complexes containing or not containing detectable inorganically bound halogen, bis(gamma-picoline)platinum dichloride, trimethylenedipyridineplatinum dichloride, dicyclopentadieneplatinum dichloride, (dimethyl sulfoxide)ethyleneplatinum(II) dichloride and products of the reaction of platinum tetrachloride with olefins and primary amines or secondary amines or primary and secondary amines, such as the product of the reaction of platinum tetrachloride dissolved in 1-octene with sec.- butylamine, or ammonium-platinum complexes as in EP-B 110,370.

The platinum catalyst is preferably employed in amounts of from 0.1 to 50 mol %, based on the number of moles of those starting materials of the formulae (11) or (2) which are present in the stoichiometric amount or less.

The reaction is preferably carried out at temperatures of from 0° C. to 110° C., preferably at pressures of from 0.05 MPa to 1.0 MPa.

If the compounds of the formulae (2), (11) or (12) should be very inert, the reaction can also be carried out at elevated temperatures, elevated pressures and in the presence of more platinum catalyst.

The reaction is preferably carried out in a solvent, which should in particular be aprotic; solvents or solvent mixtures having a boiling point or boiling range of up to 160° C., in particular of up to 120° C., in each case at 0.1 MPa (abs.), are preferred. Examples of solvents are esters, such as methyl acetate, ethyl acetate, n- and iso-propylacetate, n-, sec.- and t.-butyl acetate, ethyl formate and diethyl carbonate; ethers such as dioxane, tetrahydrofuran, diethyl ether, di-n-propyl ether, diisopropyl ether, di-n-butyl ether, ethylene glycol monomethyl ether, ethylene glycol monoethyl ether, diethylene glycol dimethyl ether and anisole; chlorinated hydrocarbons, such as dichloromethane, trichloromethane, tetrachloromethane, 1,2-dichloroethane, trichloroethylene, tetrachloroethylene and chlorobenzene; hydrocarbons, such as pentane, n-hexane, hexane isomer mixtures, cyclohexane, heptane, octane, ligroin, petroleum ether, benzene, toluene and xylenes; ketones, such as acetone, methyl ethyl ketone and methyl isobutyl ketone; carbon disulfide, pyridine, acetonitrile and nitrobenzene, or mixtures of these solvents.

The term solvent does not mean that all the reaction components must be soluble therein. The reaction can also be carried out in a suspension or emulsion of one or more reactants. The reaction can also be carried out in a solvent mixture with a miscibility gap, in which case at least one reactant is soluble in each of the mixing phases.

The compounds (11) or (2) are preferably employed in the process according to the invention in the molar ratio 1:2 to 2:1, in particular 1:1.1 to 1.1:1, compared with the compound of the formula (12).

Some of the compounds of the formulae (2), (11) and (12) are commercial products. They can be prepared from known compounds using known methods (for example as described in: Houben-Weyl-Müller, Methoden der Organischen Chemie [Methods of Organic Chemistry], Georg Thieme Verlag, Stuttgart).

The alkenyl radical is introduced into compounds of the formula (2) by, for example, reaction of the appropriate alkenyl halides with organometallic benzene derivatives, in particular with the appropriate Grignard reagents or organolithium compounds, for example 4-halophenylmagnesium halide. This reaction is usually carried out in a solvent which is inert toward the organometallic compound employed, such as diethyl ether, methyl tert.-butyl ether, tetrahydrofuran, 1,4-dioxane, hydrocarbons and mixtures thereof, such as toluene, benzene and hexane isomer mixture. It is preferably carried out at temperatures of from −100° C. to +110° C., in particular at pressures of from 0.09 to 0.11 MPa (abs.). The reaction may under certain circumstances be accelerated by ultrasound. Examples 1 and 2 were carried out in accordance with process 1.

Process 2

Compounds of the formula (8) and (1) can also be prepared by reacting compounds of the formula

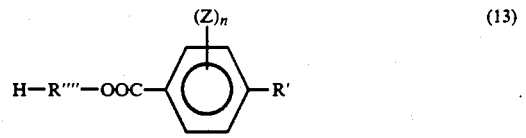  (13)

or compounds of the formula

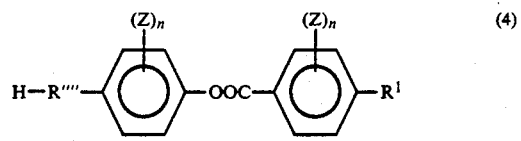  (4)

with compounds of the formula

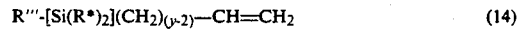 (14)

in the presence of platinum metals and/or compounds thereof, where, in the above formulae (13), (4) and (14), R', R''', R'''', R* and y are as defined above in the formula (8) and $R^1$ is as defined above in the formula (1).

Platinum metals and/or compounds thereof which can be employed are the corresponding metals and compounds mentioned under process 1.

The preferred reaction conditions, such as the amount ratios, pressures, temperatures and solvents, likewise correspond to those of process 1.

Correspondingly, that stated above regarding the starting compounds (2), (11) and (12) applies to the accessibility of the starting compounds (13) and (4) or (14).

The starting materials used for compounds of the formula (13) may also be dimethylsilylbenzoyl chlorides. These can be obtained in accordance with U.S. patent application Ser. No. 229,188 (filed on 8.8. 1988, corresponding to EP-A-304,720, F. H. Kreuzer et al., Consortium für elektrochemische Industrie GmbH) from 1,4-dihalobenzene, reacting the appropriate mono-Grignard compound with dimethylchlorosilane, carrying out a further reaction with magnesium and reacting with $CO_2$, and finally reacting the 4-dimethylsilylbenzoic acid thus obtained with, for example, thionyl chloride.

Process 3

The compounds of the formula (8) and (1) can also be prepared by
(a) reacting compounds of the formula

 (15)

or compounds of the formula

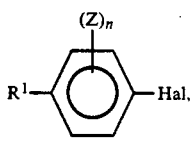

(5)

in which Hal is a halogen atom, preferably chlorine or bromine, with a metal, preferably magnesium, and reacting the resultant organometallic compound either with (b) compounds of the formula $$R'''{-}OOC{-}Hal \quad (16)$$

or $$R^2{-}OOC{-}Hal \quad (7),$$

in which Hal is as defined in the formula (15) or (5), where, in the abovementioned formulae (15), (5), (16) and (7), the radicals R' and R'', Z and n are as defined in the formula (8) and $R^1$ and $R^2$ are as defined in the formula (1).

The abovementioned reactions (a) and (b) are preferably carried out in an aprotic, essentially anhydrous solvent. Examples of such solvents are the solvents mentioned above as being suitable for process 1. In the case of the reaction with a metal, preferably magnesium, it is additionally advantageous if the solvent does not react with the metal under the reaction conditions chosen therein. For this reason, halogenated solvents should not be employed in this step.

Process 4

Process 3 can also be modified by employing compounds of the formula (16) in which the radical R'' has been replaced by a radical of the formula $$H_2C{=}CH{-}(CH_2)_{(y{-}2)}{-}R'''' \quad (18)$$

or a radical of the formula $$H{-}R''''{-} \quad (19)$$

or employing compounds of the formula (7) in which the radical $R^2$ has been replaced by a radical of the formula

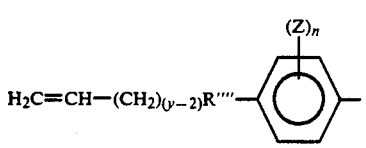

(25)

or a radical of the formula

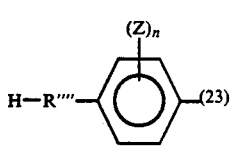

(23)

where, in the above formulae (18), (19), (23) and (25), R'''', Z, n and y are as defined in the formula (8) and the product obtained from the reaction which contains a radical of the formula (18) or (25) is subsequently treated as in process 1, and the product obtained from the reaction which contains a radical of the formula (19) or (23) is subsequently treated as in process 2.

USE

The liquid-crystalline compounds according to the invention or the liquid-crystalline compounds which can be prepared according to the invention can be used in display devices, particularly in display devices produced using smectic liquid crystal (mixtures). In this case, it is possible to use pure compounds of the formula (8) or (1), mixtures thereof and in particular mixtures of liquid-crystalline compounds of the formula (8) and/or (1) with other liquid crystals. The compounds according to the invention are suitable for the preparation of smectic mixtures, in particular for mixtures which are capable of forming a smectic C phase. However, they may also be used as additives for nematic or cholesteric phases. The compounds of the formula (8) and (1) can be used both to prepare liquid-crystalline base mixtures and to positively modify the properties of ready-prepared base mixtures—such as, for example, the optical anisotropy, the electric anisotropy, the spontaneous polarization, the viscosity, the tilt angle, the pitch and the phase behavior.

The proportion of liquid-crystalline, silylated benzoic acid derivatives according to the invention in liquid-crystal mixtures may vary within broad limits depending on the intended use. It may be, for example, from 1 percent by weight up to 100 per cent by weight.

In the examples below, unless otherwise stated,
 a) all amounts relate to the weight;
 b) all pressures are 0.10 MPa (abs.);
 c) all temperatures are 20° C.
The phase descriptions are abbreviated as follows:
 d) the numerical values denote transition temperatures, measured in °C;
 e) the phase types are characaterized as follows:
  i: isotroic phase,
  n: nematic phase,
  ch: cholesteric phase,
  sA: smectic A phase,
  sC: smectic C phase,
  sC*: chiral smectic C phase,
  sB: smectic B phase,
  s: smectric state of undetermined type,
  c: crystalline,
  G: glass state.
 f) Phase descriptions in parentheses indicate monotropic coolable phases.

The nomenclature used in the examples below for the chemical compounds does not always correspond to the International Union of Pure and Applied Chemistry (IUPAC) rules. Thus, the radical called "pentamethyldisiloxyl" group in some examples is more correctly named the pentamethyldisiloxyanyl group.

EXAMPLE 1

A 0.5% dicyclopentadienylplatinum dicloride solution in dichloromethane was added as catalyst to a solution of 4-(6-hexenyloxy)phenyl n-heptyloxybenzoate in dichloromethane, and a slight excess of trimethylsilane was passed into the refluxing mixture over the course of 14 hours. After both 8 and 12 hours, further portions of dicyclopentadienylplatinum dichloride solution were added. After complete hydrosilylation, the mixture was flushed with nitrogen, and the dichloromethane was removed by distillation under reduced pressure. The crude product was purified by chromatography on silica gel, to give 4-(6-trimethylsilylhexyloxy)phenyl 4-heptyloxy benzoate, phases: c 60 sA 70 i.

The following were prepared analogously:

4-(6-trimethylsilylhexyloxy)phenyl 4-(4-propyl-transcyclohexylene)benzoate, phases: c 92 sA 140 n 147 i.

4-(6-trimethylsilanylhexyloxy)phenyl 4-butyloxybenzoate; phases: c 81 (n 61) i 4-(5-trimethylsilylpentyloxy)phenyl 4-heptyloxybenzoate; phases: c 74 (s ? ? sA 71-72) i 4-(4-trimethylsilylbutyloxy)phenyl 4-heptyloxybenzoate; phases: c 78 (sA 56) i 4-(6-trimethylsilylhexyloxy)phenyl 4-heptyloxybenzoate; phases: c 60 sA 70 i 4-(6-trimethylsilylhexyloxy)phenyl 4-(4-propyl-transcyclohexylene)benzoate; phases: c 92 sA 140 n 14 i 4-(6-trimethylsilylhexyloxy)phenyl 4-butyloxybenzoate; phases: c 81 (n 61) i 4-(5-trimethylsilylpentyloxy)phenyl 4-heptyloxybenzoate; phases: c 74 (s ? ? sA 71-72) i 4-(4-trimethylsilylbutyloxy)phenyl 4-heptyloxybenzoate; phases: c 78 (sA 56) i 4-(6-trimethylsilylhexyloxy)phenyl [(S)-2-methylpentyloxy]-3-fluorobenzoate

EXAMPLE 2

A 0.5% strength dicyclopentadienylplatinum dichloride solution in dichloromethane was added to a solution of 4-(6-hexenyloxy)phenyl n-heptyloxybenzoate and an equimolar amount of pentamethyldisiloxane in toluene, and the resultant mixture was refluxed for 5 hours. After complete hydrosilylation, the reaction mixture was flushed with nitrogen, and the solvent was removed by distillation under reduced pressure. The crude product was purified by chromatography on silica gel, to give 4-(6-pentamethyldisiloxylhexyloxy)-phenyl 4-heptyloxybenzoate, phases: c 42 sA 67 i.

The following were prepared analogously:

4-(6-pentamethyldisiloxylhexyloxy)phenyl 4-(4-propyl-trans-cyclohexylene)benzoate, phases: c 57 sC 79 sA 139

4-(6-pentamethyldisiloxanylhexyloxy)phenyl 4-butyloxybenzoate; phases: c 64 (sA 54-56)

4-(5-pentamethyldisiloxanylpentyloxy)phenyl 4-heptyloxybenzoate; phases: c 27 sA 67 i 4-(4-pentamethyldisiloxanylbutyloxy)phenyl 4-heptyloxybenzoate; phases: c 57 (sA 49) i

What is claimed is:

1. A liquid crystalline compound of the formula

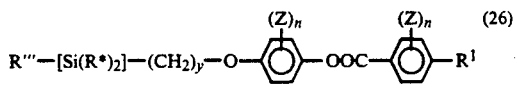

where R* is a $C_1$- to $C_{18}$-hydrocarbon radical; R''' is a radical of the formula $R^*—[Si(R^*)_2O]_v—$, where v is an integer having a value of from 1 to 10; $R^1$ is selected from the group consisting of a cyclohexyl radical, a cyclohexyl radical which is substituted by $C_1$- to $C_8$-radicals, a $C_1$- to $C_{18}$-alkyl radial, a $C_1$- to $C_{18}$-alkoxy radical, except for the n-octyloxy and n-decyloxy radicals; Z is a halogen atom which is bonded to the benzene ring in the 2-, 3-, 5- or 6-position; n is 0 or 1; and y is an integer of from 4 to 18.

2. The liquid crystalline compound of claim 1, wherein $R^1$ is a cyclohexyl radical.

3. The liquid crystalline compound of claim 1, wherein $R^1$ is a cyclohexyl radical which is substituted by $C_1$- to $C_8$-alkyl radicals.

4. The liquid crystalline compound of claim 1, wherein $R^1$ is a $C_1$- to $C_{18}$-alkyl radical.

5. The liquid crystalline compound of claim 1, wherein $R^1$ is a $C_1$- to $C_{18}$-alkoxy radical except for the n-octyloxy and n-decyloxy radicals.

6. The liquid crystalline compound of claim 1, wherein at least one n is 0.

7. A display device containing the liquid crystalline compound of claim 1.

* * * * *